United States Patent
Kniess et al.

(10) Patent No.: US 7,708,823 B2
(45) Date of Patent: *May 4, 2010

(54) SEMI-TRANSPARENT INTERFERENCE PIGMENTS CONTAINING TIN

(75) Inventors: Helge Bettina Kniess, Roβdorf (DE); Klaus Bernhardt, Groβ-Umstadt (DE); Wolf-Dietrich Weber, Pfungstadt (DE); Gerhard Pfaff, Münster (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/994,210

(22) PCT Filed: Jun. 9, 2006

(86) PCT No.: PCT/EP2006/005565

§ 371 (c)(1),
(2), (4) Date: Dec. 28, 2007

(87) PCT Pub. No.: WO2007/000232

PCT Pub. Date: Jan. 4, 2007

(65) Prior Publication Data

US 2008/0210123 A1 Sep. 4, 2008

(30) Foreign Application Priority Data

Jun. 29, 2005 (DE) .................... 10 2005 030 243

(51) Int. Cl.
*C09C 1/00* (2006.01)
*C09C 3/00* (2006.01)
*C09D 5/36* (2006.01)
*C09D 7/12* (2006.01)
*C09D 11/02* (2006.01)
*C09D 17/00* (2006.01)
*A61K 8/19* (2006.01)

(52) U.S. Cl. ............... 106/403; 106/31.9; 106/415; 106/417; 106/441; 47/57.6; 424/69; 427/215; 427/218; 428/403; 524/401; 524/413; 524/434

(58) Field of Classification Search ............... 106/403, 106/415, 417, 441, 31.9; 427/215, 218; 428/403; 47/57.6; 424/69; 524/401, 413, 434

See application file for complete search history.

(56) References Cited

U.S. PATENT DOCUMENTS

| 4,038,099 A * | 7/1977 | DeLuca et al. .......... 106/417 |
| 4,086,100 A * | 4/1978 | Esselborn et al. ........ 106/417 |
| 5,116,664 A | 5/1992 | Kimura et al. |
| 5,308,394 A | 5/1994 | Minohara et al. |
| 5,753,024 A * | 5/1998 | Vogt et al. .............. 106/417 |
| 2008/0207772 A1 * | 8/2008 | Kniess et al. ........... 514/769 |

FOREIGN PATENT DOCUMENTS

| DE | 103 31 903 A1 | 2/2004 |
| EP | 0 327 739 A | 8/1989 |
| EP | 0 450 945 A | 10/1991 |

* cited by examiner

*Primary Examiner*—Anthony J Green
(74) *Attorney, Agent, or Firm*—Millen, White, Zelano & Branigan, P.C.

(57) ABSTRACT

The present invention relates to semitransparent interference pigments having a neutral mass tone comprising a substrate and a coating comprising metallic tin and additionally at least one metal oxide, to a process for the preparation of these pigments, and to the use thereof.

23 Claims, No Drawings

SEMI-TRANSPARENT INTERFERENCE PIGMENTS CONTAINING TIN

The present invention relates to semitransparent interference pigments having a neutral mass tone comprising a substrate and a coating comprising metallic tin and additionally at least one metal oxide, to a process for the preparation of these pigments, and to the use thereof.

The use of effect pigments in a very wide variety of applications is increasing in importance. In the automobile sector, in the colouring of plastics, in cosmetics, but also in the printing sector, use is increasingly being made of effect pigments, which are intended to impart particular lustre or particular colour effects to the products pigmented therewith. In general, the effect pigments are substrates, for example comprising metals, mica or synthetic flakes of $SiO_2$, glass or $Al_2O_3$, which are coated with one or more layers, for example of metals or metal oxides. In particular, metal oxides are frequently used layer materials since they can be applied to the substrates by precipitation and are very substantially chemically inert. A common metal oxide employed is titanium dioxide. The rutile modification of titanium dioxide is the preferred modification here. In order to achieve the highest possible degree of rutilisation, the titanium dioxide layer is precipitated onto a tin dioxide layer which has already been applied. The tin dioxide controls crystallisation of the precipitated titanium dioxide layer into the rutile modification.

During the development of novel pigments having novel colour effects, the reduction of metal oxide layers in lustre pigments has also been described, for example in DE 199 53 655, DE 198 43 014, DE 198 22 046, DE 196 18 562, DE 195 11 697 or DE 195 11 696. The reducing agents employed in the said specifications are, for example, ammonia, carbon, hydrocarbons or metals. A significant disadvantage of the use of the said reducing agents is contamination of the layer reduced therewith, in particular by means of carbon, which results in undesired changes to the colour effects that are actually desired. Reduction using metals is also disadvantageous since in this way an additional component is introduced into the coating which can likewise result in undesired changes to the properties of the pigments. In addition, reduction of the titanium dioxide present as the uppermost layer takes place in the case of all pigments from the prior art, resulting in the formation of titanium suboxides having a bluish colour. These coloured suboxides are the principal aim of the reduction.

A particular example of reduction pigments are the tin-containing grey pigments described in DE 195 22 267, which are obtainable by pyrolysis of substrates coated with tin dioxide and at least one further metal oxide and colloidal organic particles. The pyrolysis here is carried out at temperatures of 900-1100° C. and with exclusion of oxygen. Although the pigments described therein exhibit a grey mass tone and silver interference, they likewise, however, exhibit a blue tinge or a yellowish to brownish coloration on tilting to flat angles. The blue tinge obtained is attributable to the formation of titanium suboxides, which, as already described above, can form in the reduction of titanium dioxide-containing layers. However, this blue tinge is frequently undesired since it distorts the silver colour impression of the articles pigmented therewith. In addition, the inclusion of colloids does not always take place completely or bleeding effects occur, i.e. the colloid is able to diffuse into a corresponding medium into which the pigment has been incorporated. Furthermore, the pigments described do not exhibit a strong lustre effect.

There is therefore a demand for novel effect pigments having a grey mass tone and silver interference which have high lustre and do not exhibit a blue coloration from any viewing angle and are thus overall colour-neutral.

The present invention accordingly relates to semitransparent interference pigments having a neutral mass tone comprising a substrate and a coating comprising metallic tin and additionally at least one metal oxide.

The pigments according to the invention exhibit high lustre, are grey and exhibit absolutely no blue tinge, irrespective of the viewing angle. In addition, they exhibit an interference with a noble appearance, for example silver. In addition, the coating comprising metallic tin is free from carbon or other impurities which originate from reduction using hydrocarbons or metals, such as, for example, lithium, sodium, calcium or other metals. In addition, bleeding effects or effects in which certain constituents of the pigments diffuse to the surface of the pigment or completely out of the pigment do not occur.

The present invention likewise relates to a process for the preparation of the interference pigments according to the invention, in which a substrate coated with a coating comprising tin dioxide and optionally additionally at least one further metal oxide is reacted in a reducing gas mixture comprising nitrogen and hydrogen with formation of metallic tin.

The pigments according to the invention can be employed in a variety of applications. The present invention therefore likewise relates to the use of interference pigments in accordance with the present invention in cosmetics, surface coatings, inks, plastics, films, in security printing, in security features in documents and identity papers, for laser marking, for colouring seed, for colouring foods or in medicament coatings and for the preparation of pigment compositions and dry preparations.

The pigments according to the invention are based on substrates, where the substrate may comprise synthetic or natural mica, phyllosilicates, glass, borosilicates, $SiO_2$, $Al_2O_3$, $TiO_2$, graphite and/or BiOCl.

In a further embodiment of the present invention, one or more layers comprising metal oxides, metal oxide hydrates, metal suboxides, metals, metal fluorides, metal nitrides, metal oxynitrides and/or mixtures thereof may be present in the pigments according to the invention between the coating comprising metallic tin and additionally at least one metal oxide and the substrate.

The metal oxide, metal oxide hydrate, metal suboxide, metal, metal fluoride, metal nitride, metal oxynitride layers or the mixtures thereof may be of low refractive index (refractive index<1.8) or high refractive index (refractive index≧1.8). Suitable metal oxides and metal oxide hydrates are all metal oxides or metal oxide hydrates to be applied as layers, such as, for example, aluminium oxide, aluminium oxide hydrate, iron oxide, tin oxide, cerium oxide, zinc oxide, zirconium oxide, chromium oxide, titanium oxide, in particular titanium dioxide, titanium oxide hydrate and mixtures thereof, such as, for example, ilmenite or pseudobrookite. Metal suboxides which can be employed are, for example, the titanium suboxides. Suitable metals are, for example, iron, chromium, aluminium, nickel, silver, gold, titanium, copper or alloys, a suitable metal fluoride is, for example, magnesium fluoride. Metal nitrides or metal oxynitrides which can be employed are, for example, the nitrides or oxynitrides of the metals titanium, zirconium and/or tantalum. Metal oxide, metal, metal fluoride and/or metal oxide hydrate layers and very particularly preferably metal oxide and/or metal oxide hydrate layers are preferably applied to the substrates. Furthermore, multilayered structures comprising high- and low-refractive-index metal oxide, metal oxide hydrate, metal or metal fluoride layers may also be present, with high- and low-refractive-index layers preferably alternating.

Particularly suitable materials of high refractive index are, for example, $TiO_2$, $ZrO_2$, ZnO, $SnO_2$ and/or mixtures thereof. $TiO_2$ is particularly preferred. The thickness of these layers here is in each case about 3 to 300 nm and preferably 20 to 200 nm.

Particularly suitable materials of low refractive index are, for example, $SiO_2$, $SiO(OH)_2$, $Al_2O_3$, AlO(OH), $B_2O_3$, $MgF_2$ and/or mixtures thereof. $SiO_2$ is particularly preferred. The thickness of the individual layers of these materials is between 3 and 300 nm, they are preferably thicker than 20 nm and up to 200 nm thick.

Overall, the materials of the additional layers should be selected and their layer thicknesses set, depending on the layer material, in such a way that the semitransparency of the pigments according to the invention is retained.

The shape and size of the substrates employed is not crucial per se. The substrates may be irregularly shaped, spherical or in flake form. Spherical substrates consist, for example, of $SiO_2$ or glass and have a diameter of 0.2 to 10 µm, preferably 0.5 to 5 µm. The substrates are preferably in flake form. Flake-form substrates generally have a thickness of between 0.05 and 5 µm, in particular between 0.1 and 4.5 µm. The size of the interference pigments in the length or width can be between 1 and 250 µm, it is preferably in the range from 2 to 200 µm and very particularly preferably in the range from 2 to 100 µm. The size of the substrates can be matched to the requirements of the particular applications.

The substrates mentioned are provided with a coating comprising metallic tin and additionally at least one metal oxide, which acts as the outer optically active layer. The layer thickness of the coating comprising metallic tin and additionally at least one metal oxide is 1 to 300 nm, preferably 1 to 100 nm. The proportion of metallic tin in the coating is 0.01 to 50% by weight, preferably 0.05 to 20% by weight and in particular 0.1 to 10% by weight, based on the coating. Tin oxide, titanium oxide, zirconium oxide and zinc oxide are suitable as at least one metal oxide. If the metallic tin in the coating is present in combination with tin oxide, this originates in the simplest embodiment from incomplete reduction in the preparation processes in accordance with the present invention. The additional metal oxide is preferably an oxide other than tin oxide. The metallic tin in the coating is very particularly preferably present in combination with titanium oxide as additional metal oxide. In addition, further simple or complex metal oxides, for example ilmenite or pseudobrookite, may be present in the tin-containing coating.

In a further embodiment, the pigments according to the invention may be provided with an additional organic coating. Examples of such coatings are given, for example, in EP 0 632 109, U.S. Pat. No. 5,759,255, DE 43 17 019, DE 39 29 423, DE 32 35 017, EP 0 492 223, EP 0 342 533, EP 0 268 918, EP 0 141 174, EP 0 764 191, WO 98/13426 or EP 0 465 805, the disclosure content of which is hereby incorporated by way of reference. In addition to the optical properties already mentioned, pigments comprising an organic coating, for example comprising organosilanes or organotitanates or organozirconates, additionally have increased stability to weathering influences, such as, for example, moisture and light, which is of particular interest, especially for industrial coatings and in the automobile sector. The stabilisation can be improved by inorganic components of the additional coating. Overall, the respective contents for the additional stabilising coating should be selected so that the optical properties of the interference pigments according to the invention are not significantly affected.

The pigments according to the invention are obtainable by reaction of a substrate coated with a coating comprising tin dioxide and optionally additionally at least one further metal oxide, in a reducing gas mixture comprising nitrogen and hydrogen with formation of metallic tin. This enables the provision of the coating comprising metallic tin and additionally at least one metal oxide.

In the simplest embodiment, only one tin dioxide-containing coating is present, which, after the processes according to the invention have been carried out, results in the formation of a coating comprising metallic tin and tin oxide. At least one further metal oxide is preferably additionally present in the tin dioxide-containing coating.

However, the reduction processes described in the prior art differ significantly in the procedure from that in accordance with the present invention. The use of the reducing gas mixture comprising nitrogen and hydrogen basically prevents contamination of the resultant layers with carbon or metals. At the same time, a blue coloration due to the formation of titanium suboxides is not observed on use of the process according to the invention, a situation which is surprising based on knowledge of the prior art.

In the process according to the invention for the preparation of the pigments described, a substrate coated with a coating comprising tin dioxide and optionally additionally at least one further metal oxide is reacted in a reducing gas mixture comprising nitrogen and hydrogen with formation of metallic tin. In this way, it is ensured that the coating comprising metallic tin is free from carbon. Tin dioxide-containing coatings which optionally additionally have at least one further metal oxide can be prepared in a manner known to the person skilled in the art, for example by precipitation from corresponding aqueous solutions which comprise a tin salt or a salt corresponding to the metal oxide additionally to be deposited. The precipitations can also be carried out in a water/solvent mixture.

The coating comprising tin dioxide and optionally additionally at least one further metal oxide is preferably in the form of separate layers of tin dioxide and at least one further metal oxide, where the layer of at least one further metal oxide is particularly preferably applied to the layer of tin dioxide. This applies in particular if the further metal oxide employed is preferably titanium dioxide. Pigments having this structure as precursor of the pigments according to the invention are known. They are effect pigments in which the tin dioxide layer usually serves for rutilisation of the subsequent titanium dioxide layer. On use of these pigments in the processes according to the invention, the tin dioxide layer thus fulfils two functions. Firstly, it ensures rutilisation of the subsequently applied titanium dioxide layer; secondly, metallic tin is formed by reduction from the applied tin dioxide on use of the processes according to the invention.

For the application of titanium dioxide, the process described in U.S. Pat. No. 3,553,001 is preferably employed. Here, an aqueous solution of an inorganic titanium salt is slowly added to a suspension, heated to about 50-100° C., in particular 70-80° C., of the substrates, optionally already precoated, and the pH is kept substantially constant at 0.5 to 5, in particular about 1.5 to 2.5, by simultaneous metered addition of a base. As soon as the desired layer thickness of the $TiO_2$ oxide hydrate has been reached, the addition of the titanium salt solution and the base is stopped. This process is also known as the titration process and has the peculiarity that an excess of titanium salt is not present, but instead only an amount as is necessary for uniform coating with the hydrated $TiO_2$ and can also be taken up by the surface of the substrate to be coated is always present per time unit. Hydrated titanium dioxide particles, which are not deposited on the surface to be coated, are therefore not present in the solution.

The reducing gas mixture comprising nitrogen and hydrogen to be employed for the reaction has a hydrogen content in the range from 2.5 to 25% by vol., in particular from 4 to 10% by vol., and very particularly preferably from 5 to 8% by vol.

The reduction of the coating comprising tin dioxide and at least one further metal oxide is carried out at temperatures of 500 to 1200° C., preferably 600 to 100° C. and particularly preferably 700 to 900° C. The calcination duration is 15-240 minutes, preferably 30-120 minutes and in particular 30-90 minutes.

In addition, in a process which is likewise according to the invention, an organic coating may additionally be applied as the outer layer. Examples of coating methods of this type are given, inter alia, in EP 0 632 109, U.S. Pat. No. 5,759,255, DE 43 17 019, DE 39 29 423, DE 32 35 017, EP 0 492 223, EP 0 342 533, EP 0 268 918, EP 0 141 174, EP 0 764 191, WO 98/13426 or EP 0 465 805. Examples of organic coatings and the advantages associated therewith have already been described above under build-up of the pigments according to the invention. The process step of application of the organic coating can be carried out directly after the other steps of the process according to the invention. The substances applied here comprise merely a proportion by weight of 0.1 to 5% by weight, preferably 0.5 to 3% by weight, of the pigment as a whole.

The interference pigments according to the invention are versatile and can be employed in many areas. Accordingly, the present invention likewise relates to the use of the pigments according to the invention in cosmetics, surface coatings, inks, plastics, films, in security printing, in security features in documents and identity papers, for colouring seed, for colouring foods or in medicament coatings, for laser marking and for the preparation of pigment compositions and dry preparations.

In the case of cosmetics, the interference pigments according to the invention are particularly suitable for products and formulations of decorative cosmetics, such as, for example, nail varnishes, colouring powders, lipsticks or eye shadows, soaps, toothpastes, etc. The interference pigments according to the invention can of course also be combined in the formulations with cosmetic raw materials and assistants of all types. These include, inter alia, oils, fats, waxes, film formers, preservatives and assistants which generally determine the applicational properties, such as, for example, thickeners and Theological additives, such as, for example, bentonites, hectorites, silicon dioxide, Ca silicates, gelatine, high-molecular-weight carbohydrates and/or surface-active assistants, etc. The formulations comprising interference pigments according to the invention may belong to the lipophilic, hydrophilic or hydrophobic type. In the case of heterogeneous formulations having discrete aqueous and non-aqueous phases, the particles according to the invention may be present in each case only one of the two phases or alternatively distributed over both phases.

The pH values of the aqueous formulations can be between 1 and 14, preferably between 2 and 11 and particularly preferably between 5 and 8. The concentrations of the interference pigments according to the invention in the formulation are not subject to any limits. They can be—depending on the application—between 0.001 (rinse-off products, for example shower gels) and 99% (for example lustre-effect articles for particular applications). The interference pigments according to the invention may furthermore also be combined with cosmetic active compounds. Suitable active compounds are, for example, insect repellents, UV A/BC protection filters (for example OMC, B3, MBC), antiageing active compounds, vitamins and derivatives thereof (for example vitamins A, C, E, etc.), self-tanning agents (for exampie DHA, erythrulose, inter alia), and further cosmetic active compounds, such as, for example, bisabolol, LPO, ectoin, emblica, allantoin, bioflavonoids and derivatives thereof.

In the case of the use of the interference pigments in surface coatings and inks, all areas of application known to the person skilled in the art are possible, such as, for example, powder coatings, automobile paints, printing inks for gravure, offset, screen or flexographic printing, and for surface coatings in outdoor applications. The surface coatings and inks here may be, for example, radiation-curing, physically drying or chemically curing. For the preparation of printing inks or liquid surface coatings, a multiplicity of binders, for example based on acrylates, methacrylates, polyesters, polyurethanes, nitrocellulose, ethylcellulose, polyamide, polyvinyl butyrate, phenolic resins, maleic resins, starch or polyvinyl alcohol, amino resins, alkyd resins, epoxy resins, polytetrafluoroethylene, polyvinylidene fluorides, polyvinyl chloride or mixtures thereof, is suitable, in particular water-soluble types. The surface coatings can be powder coatings or water- or solvent-based coatings, where the choice of coating constituents is subject to the general knowledge of the person skilled in the art. Common polymeric binders for powder coatings are, for example, polyesters, epoxides, polyurethanes, acrylates or mixtures thereof.

In addition, the interference pigments according to the invention can be used in films and plastics, for example in agricultural sheeting, infrared-reflective films and sheets, gift foils, plastic containers and mouldings for all applications known to the person skilled in the art. Suitable plastics for the incorporation of the interference pigments according to the invention are all common plastics, for example thermosets or thermoplastics. The description of the possible applications and plastics which can be employed, processing methods and additives are given, for example, in RD 472005 or in R. Glausch, M. Kieser, R. Maisch, G. Pfaff, J. Weitzel, Perlglanzpigmente [Pearlescent Pigments], Curt R. Vincentz Verlag, 1996, 83 ff., the disclosure content of which is incorporated herein.

In addition, the interference pigments according to the invention are also suitable for use in security printing and in security-relevant features for, for example, counterfeiting-proof cards and identity papers, such as, for exampie, entry tickets, staff identity cards, banknotes, cheques and cheque cards, and for other counterfeiting-proof documents. In the agricultural sector, the interference pigments can be used for colouring seed and other starting materials, in addition in the foods sector for pigmenting foods. The interference pigments according to the invention can likewise be employed for pigmenting coatings in medicaments, such as, for example, tablets or dragees.

All known thermoplastics, as described, for example, in Ullmann, Vol. 15, pp. 457 ff., Verlag VCH, can be used for laser marking using the interference pigments according to the invention. Suitable plastics are, for example, polyethylene, polypropylene, polyamides, polyesters, polyester-esters, polyether-esters, polyphenylene ether, polyacetal, polybutylene terephthalate, polymethyl acrylate, polyvinyl acetate, polystyrene, acrylonitrile-butadiene-styrene, acrylonitrile-styrene-acrylate, polycarbonate, polyether sulfones, polyether ketones and copolymers and/or mixtures thereof.

The interference pigments according to the invention are incorporated into the thermoplastic by mixing the plastic granules with the interference pigment and then shaping the mixture under the action of heat. During incorporation of the interference pigments, adhesives, organic polymer-compatible solvents, stabilisers and/or surfactants which are temperature-stable under the working conditions, all of which are known to the person skilled in the art, can be added to the plastic granules. The pigmented plastic granules are generally produced by introducing the plastic granules into a suitable mixer, wetting the granules with any additives and then adding and mixing in the interference pigment. The mixture obtained in this way can then be processed directly in an extruder or injection-moulding machine. The marking is subsequently carried out using suitable radiation.

During the marking, use is preferably made of high-energy radiation, generally in the wavelength range from 157 to 10,600 nm, in particular in the range from 300 to 10,600 nm. Mention may be made here by way of example of $CO_2$ lasers (10,600 nm), Nd:YAG lasers (1064 or 532 nm) or pulsed UV lasers (excimer lasers). The excimer lasers have the following wavelengths: $F_2$ excimer laser (157 nm), ArF excimer laser (193 nm), KrCl excimer laser (222 nm), KrF excimer laser (248 nm), XeCl excimer laser (308 nm), XeF excimer laser (351 nm), frequency-multiplied Nd:YAG lasers having wavelengths of 355 nm (frequency-tripled) or 265 nm (frequency-quadrupled). Particular preference is given to the use of Nd:YAG lasers (1064 or 532 nm) and $CO_2$ lasers. The energy densities of the lasers employed are generally in the range from 0.3 mJ/cm$^2$ to 50 J/cm$^2$, preferably 0.3 mJ/cm$^2$ to 10 J/cm$^2$.

The laser inscription is carried out by bringing the test specimen into the ray path of a pulsed laser, preferably a $CO_2$ or Nd:YAG laser. Furthermore, inscription using an excimer laser, for example via a mask technique, is possible. However, the desired results can also be achieved using other conventional types of laser which have a wavelength in a region of high absorption of the laser light-absorbent substance used. The marking obtained is determined by the irradiation time (or number of pulses in the case of pulsed lasers) and irradiation power of the laser and of the plastic system or coating system used. The power of the lasers used depends on the particular application and can readily be determined by the person skilled in the art in each individual case.

On use of pulsed lasers, the pulse frequency is generally in the range from 1 to 30 kHz. Corresponding lasers which can be employed in the process according to the invention are commercially available.

The interference pigments according to the invention can be used for laser marking in all above-mentioned plastics. The plastics pigmented in this way can be used as mouldings in the electrical, electronics and motor vehicle industries. A further important area of application for laser inscription is in identity cards and plastic marks for the individual tagging of animals. The proportion of interference pigments in the plastic is 0.01 to 10% by weight, preferably 0.05 to 5% by weight and in particular 0.1 to 3% by weight in the case of laser marking in the applications. The labelling and inscription of casings, lines, key caps, ornamental strips and functional parts in the heating, ventilation and cooling sectors or switches, plugs, levers and handles which consist of the plastics pigmented with the pigments according to the invention can be carried out with the aid of laser light even in places which are difficult to access. The markings are distinguished by the fact that they are wipe- and scratch-resistant, are stable during subsequent sterilisation processes and can be applied in a hygienically clean manner during the marking process.

In the above-mentioned areas of application, the interference pigments according to the invention are likewise suitable for use in blends with all known organic or inorganic dyes and/or pigments. Organic pigments and dyes are, for example, monoazo pigments, disazo pigments, polycyclic pigments, cationic, anionic or nonionic dyes. Inorganic dyes and pigments are, for example, white pigments, coloured pigments, black pigments or effect pigments. Examples of suitable effect pigments are metal-effect pigments, pearlescent pigments or interference pigments, which are generally based on mono- or multicoated flakes based on mica, glass, $Al_2O_3$, $Fe_2O_3$, $SiO_2$, etc. Examples of structures and particular properties of the said pigments are given, for example, in RD 471001 or RD 472005, the disclosure content of which is hereby incorporated into the present invention by way of reference. In addition, further colorants which are suitable for blending with the pigments according to the invention are luminescent dyes and/or pigments and holographic pigments or LCPs (liquid crystal polymers). The pigments according to the invention can be mixed in any ratio with commercially available pigments and fillers.

Fillers which may be mentioned are, for example, natural and synthetic mica, nylon powder, pure or filled melamine resins, talc, glasses, kaolin, oxides or hydroxides of aluminium, magnesium, calcium, zinc, BiOCl, barium sulfate, calcium sulfate, calcium carbonate, magnesium carbonate, carbon, and physical or chemical combinations of these substances. There are no restrictions regarding the particle shape of the filler. It can be, for example, flake-form, spherical or needle-shaped in accordance with requirements.

The interference pigments according to the invention are furthermore suitable for the preparation of flowable pigment compositions and dry preparations comprising one or more particles according to the invention, binders and optionally one or more additives. Dry preparations are also taken to mean preparations which comprise 0 to 8% by weight, preferably 2 to 8% by weight, in particular 3 to 6% by weight, of water and/or a solvent or solvent mixture. The dry preparations are preferably in the form of pellets, granules, chips, sausages or briquettes and have particle sizes of 0.2-80 mm. The dry preparations are used, in particular, in the preparation of printing inks and in cosmetic formulations.

The complete disclosure content of all patent applications, patents and publications mentioned above is present in this application by way of reference.

The examples below are intended to explain the invention in greater detail, but without restricting it.

EXAMPLES

Example 1

100 g of mica having a particle size of 10-60 μm are heated to 75° C. with stirring in 1.9 l of demineralised water. The pH of the suspension is adjusted to 1.8 using 5% hydrochloric acid. This is followed by metered addition of a tin tetrachloride solution (comprising 3 g of $SnCl_4.5H_2O$ and 10 ml of concentrated hydrochloric acid in 90 ml of demineralised water), during which the pH is kept constant by simultaneous dropwise addition of a 32% sodium hydroxide solution. A 30% titanium tetrachloride solution (180 g of $TiCl_4$ solution w=60%, dissolved in 180 g of demineralised water) is then added, during which the pH is kept constant by simultaneous dropwise addition of a 32% sodium hydroxide solution. The product is filtered off, washed, dried and reduced at 850° C. in a gas mixture comprising nitrogen and hydrogen (proportion of hydrogen: 8% by vol.), giving a pigment comprising metallic tin which has silver interference, a colour-neutral grey mass tone and high lustre.

Example 2

100 g of mica having a particle size of 10-60 μm are heated to 75° C. with stirring in 1.9 l of demineralised water. The pH of the suspension is adjusted to 3.0 using 10% hydrochloric acid. 35 g of a 30% $FeCl_3$ solution are then metered in, during which the pH is kept constant by simultaneous dropwise addition of 32% sodium hydroxide solution. The pH of the suspension is then adjusted to 1.8 using 5% hydrochloric acid. This is followed by metered addition of a tin tetrachloride solution (comprising 3 g of $SnCl_4.5H_2O$ and 10 ml of concentrated hydrochloric acid in 90 ml of demineralised water), during which the pH is kept constant by simultaneous dropwise addition of a 32% sodium hydroxide solution. A 30% titanium tetrachloride solution (160 g of $TiCl_4$ solution w=60%, dissolved in 160 g of demineralised water) is then added, during which the pH is kept constant by simultaneous dropwise addition of a 32% sodium hydroxide solution. The product is filtered off, washed, dried and reduced at 850° C. in a gas mixture comprising nitrogen and hydrogen (proportion of hydrogen: 8% by vol.), giving a lustrous pigment comprising metallic tin which has silver interference, a colour-neutral grey mass tone and a high hiding power.

Comparative Example (According to DE 198 43 014)

100 g of mica having a particle size of 10-60 μm are heated to 75° C. with stirring in 2 l of demineralised water. The pH of the suspension is adjusted to 1.8 using 5% hydrochloric acid. This is followed by metered addition of a tin tetrachloride solution (comprising 3 g of $SnCl_4.5H_2O$ and 10 ml of concentrated hydrochloric acid in 90 ml of demineralised water), during which the pH is kept constant by simultaneous dropwise addition of a 32% sodium hydroxide solution. A 30% titanium tetrachloride solution (180 g of $TiCl_4$ solution w=60%, dissolved in 180 g of demineralised water) is then added, during which the pH is kept constant by simultaneous dropwise addition of a 32% sodium hydroxide solution. The product is filtered off, washed, dried and calcined at 850° C. in an air atmosphere. 100 g of the resultant $TiO_2$ pigment are mixed with 3 g of silicon powder and 1 g of $CaCl_2$ and subsequently calcined at 800° C. for 30 minutes under a nitrogen atmosphere, giving a pigment which has silver interference and a blue mass tone.

Laser Marking:

PP granules (PP-HD, Stamylan PPH 10 from DSM) are processed by injection moulding by addition of 0.1% by weight of the pigment from Example 1. The moulding obtained (platelet) is subsequently inscribed using an SHT-Nd:YAG laser. At a pulse frequency of 2.5 kHz and a writing speed of 300 mm/s, the platelets exhibit a black, high-contrast and abrasion-resistant inscription. With increasing energy density, the inscription becomes increasingly darker.

The invention claimed is:

1. Semitransparent interference pigments having a neutral mass tone comprising a substrate and a coating comprising metallic tin and additionally at least one metal oxide, which coating is free from carbon, wherein the coating is in the form of
    a single layer, or
    two separate layers, wherein the first layer comprises tin and the second layer comprises at least one metal oxide, wherein the second layer is on top of the first layer.

2. Interference pigments according to claim 1, obtained by a process comprising reaction of a substrate coated with a coating comprising tin dioxide and optionally at least one further metal oxide, in a reducing gas mixture comprising nitrogen and hydrogen with formation of metallic tin.

3. Interference pigments according to claim 1, wherein the proportion of metallic tin in the coating is 0.01 to 50% by weight, based on the coating comprising metallic tin and additionally at least one metal oxide.

4. Interference pigments according to claim 1, wherein the metal oxide additionally present is titanium oxide.

5. Interference pigments according to claim 1, wherein the substrate comprises titanium oxides, synthetic or natural mica, phyllosilicates, glass, $SiO_2$, $Al_2O_3$, graphite and/or BiOCl.

6. Interference pigments according to claim 1, wherein one or more layers comprising metal oxides, metal oxide hydrates, metal suboxides, metals, metal fluorides, metal nitrides, metal oxynitrides and/or mixtures thereof are additionally present between the coating comprising metallic tin and additionally at least one metal oxide and the substrate.

7. Interference pigments according to claim 1, which are furthermore provided with an additional organic coating as an outer layer.

8. Semitransparent interference pigments having a neutral mass tone according to claim 1, comprising a substrate and a coating consisting of metallic tin and additionally at least one metal oxide.

9. Semitransparent interference pigments having a neutral mass tone according to claim 1, comprising a substrate and a coating consisting essentially of metallic tin and additionally at least one metal oxide.

10. Interference pigments according to claim 8, wherein the proportion of metallic tin in the coating is 0.01 to 50% by weight, based on the coating comprising metallic tin and additionally at least one metal oxide.

11. Interference pigments according to claim 9, wherein the proportion of metallic tin in the coating is 0.01 to 50% by weight, based on the coating comprising metallic tin and additionally at least one metal oxide.

12. Interference pigments according to claim 1, wherein the coating is in the form of a single layer.

13. Interference pigments according to claim 1, wherein the coating is in the form of two separate layers.

14. A method for imparting luster or a color effect on cosmetics, surface coatings, inks, plastics, films, security printings, security features in documents or identity papers, or for colouring seed, for colouring foods or imparting luster or a color effect on medicament coatings, or for laser marking or for the preparation of pigment compositions and dry preparations, comprising incorporating an interference pigment of claim 1.

15. A method according to claim 14, wherein the interference pigments are in the form of a blend with organic or inorganic dyes and/or pigments.

16. A process for preparing interference pigments according to claim 1, comprising reacting a substrate coated with a coating comprising tin dioxide and optionally additionally at least one further metal oxide in a reducing gas mixture comprising nitrogen and hydrogen with formation of metallic tin.

17. A process for preparing semitransparent interference pigments having a neutral mass tone comprising a substrate and a coating comprising metallic tin and additionally at least one metal oxide, which coating is free from carbon, comprising reacting a substrate coated with a coating comprising tin dioxide and optionally additionally at least one further metal oxide in a reducing gas mixture comprising nitrogen and hydrogen with formation of metallic tin.

18. A process according to claim 17, wherein the coating comprising tin dioxide and optionally additionally at least one further metal oxide is in the form of separate layers of tin dioxide and at least one further metal oxide.

19. A process according to claim 18, wherein the layer of at least one further metal oxide is applied to the layer of tin dioxide.

20. A process according to claim 17, wherein the further metal oxide is titanium dioxide.

21. A process according to claim 17, wherein the proportion of hydrogen in the gas mixture comprising nitrogen and hydrogen is 2.5 to 25% by vol.

22. A process according to claim 17, wherein the reduction is carried out at temperatures of 500-1200° C.

23. A process according to claim 17, wherein an organic coating is additionally applied as an outer layer.

\* \* \* \* \*